(12) United States Patent
Von Behren et al.

(10) Patent No.: US 7,097,619 B2
(45) Date of Patent: *Aug. 29, 2006

(54) ELEVATION BEAM PATTERN VARIATION FOR ULTRASOUND IMAGING

(75) Inventors: Patrick L. Von Behren, Bellevue, WA (US); Paul D. Freiburger, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 182 days.

This patent is subject to a terminal disclaimer.

(21) Appl. No.: 10/403,259

(22) Filed: Mar. 31, 2003

(65) Prior Publication Data

US 2004/0044284 A1 Mar. 4, 2004

Related U.S. Application Data

(63) Continuation-in-part of application No. 10/234,004, filed on Sep. 3, 2002, now Pat. No. 6,733,453.

(51) Int. Cl.
*A61B 8/00* (2006.01)
(52) U.S. Cl. .................................................. 600/447
(58) Field of Classification Search ................ 600/437, 600/440, 441, 443, 447, 458; 128/916
See application file for complete search history.

(56) References Cited

U.S. PATENT DOCUMENTS

| | | | |
|---|---|---|---|
| 5,301,168 A * | 4/1994 | Miller | 367/138 |
| 5,546,946 A | 8/1996 | Souquet | |
| 5,653,235 A | 8/1997 | Teo | |
| 5,678,554 A | 10/1997 | Hossack et al. | |
| 5,897,501 A | 4/1999 | Wildes et al. | |
| 5,902,242 A | 5/1999 | Ustuner et al. | |
| 5,911,221 A * | 6/1999 | Teo | 600/447 |
| 6,043,589 A | 3/2000 | Hanafy | |
| 6,057,632 A | 5/2000 | Ustuner | |
| 6,132,375 A | 10/2000 | Napolitano | |
| 6,340,348 B1 | 1/2002 | Krishnan et al. | |
| 6,464,638 B1 * | 10/2002 | Adams et al. | 600/443 |
| 6,511,426 B1 * | 1/2003 | Hossack et al. | 600/437 |
| 6,524,247 B1 * | 2/2003 | Zhao et al. | 600/437 |
| 6,527,720 B1 | 3/2003 | Ustuner et al. | |
| 6,733,453 B1 * | 5/2004 | Freiburger et al. | 600/447 |
| 2004/0092817 A1 * | 5/2004 | Brock-Fisher | 600/431 |

* cited by examiner

*Primary Examiner*—Francis J. Jaworski (57) ABSTRACT

Methods and systems vary the elevation beam pattern during an imaging session. A user based or automatic search mode is provided where one or more elevation beam thicknesses are used, and then a diagnosis mode is provided where an optimal or narrow elevation beam thickness is used for continued imaging. 1.25, 1.5, 1.75 and 2D arrays are used to obtain frames of data responsive to the varied elevation beam pattern.

33 Claims, 2 Drawing Sheets

ELEVATION BEAM PATTERN VARIATION FOR ULTRASOUND IMAGING

REFERENCE TO RELATED APPLICATION

The present patent document is a continuation-in-part of U.S. Pat. No. 6,733,453, filed Sep. 3, 2002, which is hereby incorporated herein by reference.

BACKGROUND

The present invention relates to ultrasound imaging with multi-dimensional transducer arrays. Multi-dimensional transducer arrays may provide an adjustable narrow elevation focus. For example, 1.25D, 1.5D or 1.75D arrays are used to acquire data representing a scan plane. Rows of elements along the elevation dimension are used to electronically or mechanically focus the transmitted energy in the elevation dimension, increasing resolution. For different imaging frequencies, different elevation thicknesses may be provided.

BRIEF SUMMARY

The present invention is defined by the following claims, and nothing in this section should be taken as a limitation on those claims. By way of introduction, the preferred embodiments described below include methods and systems for varying the elevation beam pattern during an imaging session. For example, a user or automatic search mode is provided where one or more elevation beam thicknesses are used, and then a diagnosis mode is provided where an optimal or narrow elevation beam thickness is used for continued imaging.

In a first aspect, a method for ultrasound imaging with a multi-dimensional transducer array is provided. At least a first scan line relative to the multi-dimensional transducer array is scanned in response to a first elevation beam pattern, and at least the first scan line is scanned in response to a second elevation beam pattern, the second elevation beam pattern different than the first elevation beam pattern. Both scans occur during a same scanning session.

In a second aspect, a system for ultrasound imaging with different elevation beam patterns is provided. A beamformer connects with a multi-dimensional transducer array. The beamformer is operable to form a first beam in response to a first elevation beam pattern where the first beam emanates from the multi-dimensional transducer array at a first location and first angle within a plane. The beamformer is operable to form a second beam in response to a second elevation beam pattern where the second beam emanates from the multi-dimensional transducer array at the first location and first angle in the plane. The first and second beams are formed during a single imaging session, and the first elevation beam pattern is different than the second elevation beam pattern.

In a third aspect, another method for ultrasound imaging with a multi-dimensional transducer array is provided. The multi-dimensional transducer array is positioned adjacent to a target area. Acoustic energy is transmitted for a planar area with the multi-dimensional transducer array during the array be adjacent the target area. An elevation beam pattern is varied during the transmission for sequential transmissions to the planar area.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Multi-dimensional transducer arrays are used for one or both of varying elevation beam patterns and compounding. Section I below discloses embodiments for varying the elevation beam pattern. Section II below discloses embodiments for compounding to reduce speckle and is a repetition of application Ser. No. 10/234,004, filed Sep. 3, 2002. The compounding disclosure of Section II includes techniques that result in different elevation beam patterns, such as providing different elevation beam widths as a function of the elevation aperture. As the elevation aperture varies within an imaging session, the elevation beam width varies at least at the face of the transducer.

I. Elevation Beam Pattern Variation Embodiment

Mutlti-dimensional transducer arrays allow for electronically controlling elevation beam patterns. For example, the thickness of acoustic beams adjacent the transducer (i.e. elevation aperture size) and/or the thickness of acoustic beams at a focal region are set as a function of the elevation aperture size, elevation apodization profile and/or elevation delay (e.g. elevation focus) profile. By using different elevation beam patterns for sequential scans within a same imaging session, various forms of diagnostic assistance may be provided.

In the embodiments shown above, the variation in the elevation aperture, such as left and right or side and full elevation apertures, results in different elevation beam thickness at the face of the transducer. With a same focal and apodization profiles for each aperture, the elevation beam pattern also varies away from the face of the transducers, such as near the focal region, due to the different elevation aperture extent. Variations in the focal and/or apodization profiles with a same or different aperture may also result in different elevation beam patterns.

Figure 4:
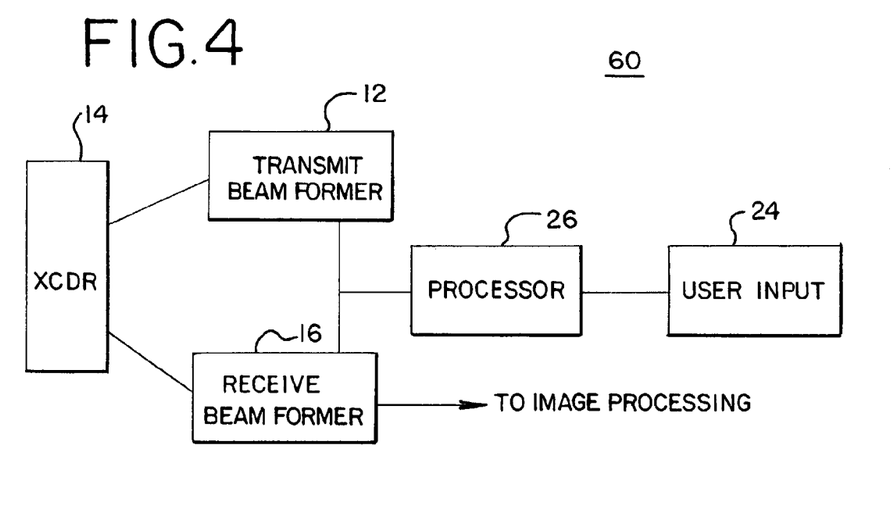
FIG. 4 is a block diagram of one embodiment of an ultrasound system for varying elevation beam patterns.

A system 60 for ultrasound imaging with different elevation beam patterns is provided in one embodiment and shown in FIG. 4. The system 60 includes a multi-dimensional transducer array 14, a transmit beamformer 12, a receive beamformer 16, a user input 24 and a processor 26. The system 10 described below with respect to FIG. 1 or another system with additional, different or fewer components may be used. For example, the system 60 for applying different elevation beam patterns within a scanning session is either operable to also provide the elevation compounding discussed below or operable without the elevation compounding discussed below. Some of the components of the system 60 are further described in the FIG. 1 discussion below.

The elevation beam pattern variation is implemented in one or both of the transmit and receive beamformers 12, 16 with analog and/or digital components. The transmit beamformer 12 includes one or more waveform generators, memories, oscillators, transistors, amplifiers and delays in a plurality of channels associated with a respective plurality of elements of the array, including elevation spaced elements. Waveforms with different amplitudes are generated and applied to elevation spaced elements. The waveforms are also delayed relative to each other. The receive beamformer 16 includes one or more filters, delays, amplifiers and a summer. Signals received from different elevation spaced elements (i.e. receive channels) are amplified and delayed relative to each other and then summed.

The transmit and receive beamformers 12, 16 connect with the multidimensional transducer array 14. For example, a multiplexer switchably connects different beamformer channels to different elements. The transmit and receive beamformers 12, 16 are operable to form different acoustic beams in response to different elevation beam patterns. The elevation based relative delays, selected aperture, transmit frequency and/or apodization on either or both of transmit and receive provide different elevation beam patterns. For example, one beam pattern has a different elevation beam thickness at a focal region than another beam pattern. The maximum and minimum elevation beam thickness is a function of the transducer array 14. For example, a transducer array with three spaced rows of elements in one embodiment is operable to provide 3 mm to 3 cm −6 dB width at a focal point at 5–10 cm of depth. Any of various ranges, depths and elevation apertures may be used.

In one embodiment, the different elevation beam patterns are used for sequential scans of a substantially same plane. Substantially the same plane is used to account for transducer motion due to unintentional or intentional movement by the sonographer or movement of the patient. For example, the transmit and receive beamformers 12, 16 generate acoustic beams of one elevation thickness at a given distance from the transducer (e.g. the focal region) for a first complete scan of a two-dimensional region and then generate acoustic beams of a different elevation thickness at the given distance from the transducer for a second complete scan of the two-dimensional region. As yet another example, the transmit beamformer 12 emanates a first beam from the multi-dimensional transducer array 14 at a first location and first angle within the scan plane and later emanates a second beam from the multi-dimensional transducer array at the first location and first angle in the plane. The first and second beams are at a same position relative to the transducer array 14. Where there is no movement, the first and second beams are at a same position within a patient, but may have a different thickness within the patient.

The transmit and receive beamformers 12, 16 apply the different elevation beam patterns during a single imaging or scanning session. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. Generally, the transducer is maintained adjacent to the patient for major portions or the entire duration of the imaging session.

In one embodiment, the transmit and receive beamformers 12, 16 are responsive to a search mode. In response to user input or the system automatically initiating the search mode, instructions are provided to the transmit and receive beamformers 12, 16 for search mode operation. The elevation beam pattern varies or is changed in response to and/or during the search mode operation. The search mode provides searching for one or both of an object within the patient and an optimal elevation beam pattern. For example, a wider or thicker elevation beam pattern is used to allow a user to search for an object within the patient. As another example, various elevation beam patterns are used and a more optimal elevation beam pattern is selected in response to user input or automatic calculation. After completion of the search mode (e.g. the object is located or the system identifies a desired elevation beam pattern), the transmit and receive beamformers 12, 16 enter a diagnosis mode. In the diagnosis mode, the transmit and receive beamformers 12, 16 use a different (e.g. narrower) or selected elevation beam pattern for diagnostic or continued imaging.

The user input 24 is one or more of various user input devices, such as a trackball, mouse, touch pad, joystick, button, keyboard, slider, rotatable knob or other now known or later developed input device. The user operates the user input 24 to initiate a search mode, to control the elevation beam pattern (e.g. adjust a slider or knob to make the elevation beam pattern more or less concave or convex), to end the search mode and/or to select an elevation beam pattern. Alternatively, the transmit and receive beamformers 12, 16 are operable to automatically vary between different elevation beam patterns without user input.

The processor 26 is one or more of digital signal processor, application specific integrated circuit, a general processor, control processor, analog circuit, a digital circuit, combinations thereof or other now known or later developed processor. The processor 26 controls the transmit and receive beamformers 12, 16. For an automatic variation of the elevation beam pattern or for an automatic search for the optimal elevation beam pattern, the processor 23 is operable to calculate parameter values responsive to different elevation beam patterns. The more optimal elevation beam pattern is selected as a function of the parameter values. Subsequent beams, such as transmitted for diagnostic imaging, are formed based on the selected elevation beam pattern. The parameter is calculated from data before or after a detector or estimator.

Figure 5:
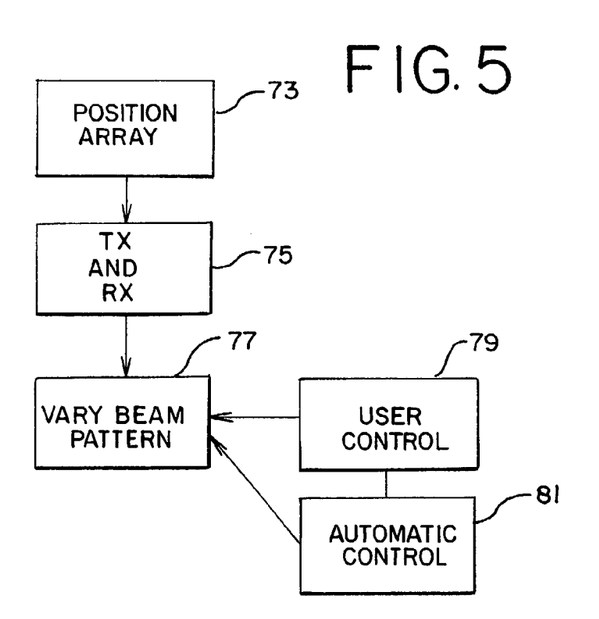
FIG. 5 is a flowchart diagram of one embodiment of a method for varying the elevation beam pattern.

FIG. 5 shows a method of one embodiment for ultrasound imaging with the multi-dimensional transducer array 14. Different elevation beam patterns, such as elevation beam thicknesses, are used during a single imaging session or while the multi-dimensional transducer array is positioned adjacent to or in a patient. Different, additional or fewer acts may be provided.

In act 73, the multi-dimensional transducer array 14 is positioned adjacent to a target area. The target area is a region of a patient to be scanned, such as a region to be biopsied, an organ of interest, an object of interest (e.g., tumor or cyst) or a vascular structure. Where the multi-dimensional transducer array 14 is adapted for use on the skin of a patient, the user holds the transducer array 14 adjacent to the patient on the skin. Where the multi-dimensional transducer array 14 is adapted for use within the patient, such as on a catheter or endocavity probe, the transducer array 14 is positioned within the patient. The transducer array 14 is maintained adjacent to the target area while being held in one position or while being moved around to search for a particular region of interest within the target area.

In act 75, acoustic energy is transmitted and echo signals received with the multi-dimensional transducer array 14. The acoustic energy is transmitted to and received from a planar area, but single scan lines (i.e. one dimensional imaging—CW Doppler or M-mode) or volume spaced scan lines may be used. The acoustic energy is transmitted and echoes received during an imaging session, such as while the multi-dimensional transducer array 14 is maintained adjacent to the target area.

In act 77, the elevation beam pattern is varied for sequential scans of the target area. For example, the elevation beam pattern is varied for different transmissions to a substantially same planar area, scan line and/or volume scan. The different elevation beam patterns are used during the same scanning or imaging session and/or while the transducer is maintained adjacent the target area. The transmit and receive beamformers 12, 16 scan along at least a first scan line relative to the multidimensional transducer array 14 in response to a first elevation beam pattern. For example, a wide elevation beam pattern is provided in a search mode to allow the user to more quickly identify a particular object or region. A wider elevation slice thickness includes information from a greater volume of the target area. The scan plane thickness is then varied for a subsequent or sequential scan of the scan plane or target area. The transmit and receive beamformers 12, 16 then scan along at least the first scan line in response to a different elevation beam pattern. For example, a narrow elevation beam pattern or an optimal elevation beam pattern is provided in a diagnosis mode before or after the search mode. The narrow elevation beam pattern may provide better resolution. An optimal elevation beam pattern may provide better resolution without loosing desired wall or border information.

Any of various combinations of elevation beam patterns are used during an imaging session. For example, at least three different elevation beam thicknesses for subsequent scans are used. As another example, different elevation apertures are used for different elevation beam patterns. The transmit and receive delay, apodization and apertures may be different or the same for a given transmit and receive combination or scan.

The compounding discussion below in Section II notes several combinations of different elevation apertures, resulting in different beam patterns for different scans and in different elevation thicknesses at least at the face of the transducer array. In one embodiment, a same elevation aperture is used with different delays and/or apodization, providing different elevation beam thicknesses over a portion of or entire scan line depth.

In optional act 79, the elevation beam pattern varies in response to user input. The user controls the elevation beam pattern, such as instructing a change from one elevation beam thickness to another elevation beam thickness. The user varies the elevation beam pattern through a range of patterns. The user then selects the most desirable elevation beam pattern for imaging. Subsequent imaging during the scanning session is generated in response to the user selected elevation beam thickness or pattern.

In optional act 81, the elevation beam pattern varies automatically. Acts 79 and 81 are alternative embodiments, but may both be available in a single system 10. Alternatively, the user adjusts an automatic selection or vice versa. In 81, the transmit and receive beamformers 12, 16 automatically scan with different elevation beam patterns during an imaging session, such as a different elevation beam patterns based on a two-way response subsequent scans using either the same or different patterns for the transmit and responsive receive operations. After user initiation of the automatic variation, the elevation beam pattern is varied independent of user input. In alternative embodiments, the system 10 initiates the automatic variation and/or further user input selects an elevation beam pattern during the automatic variation.

Pre-detected data, detected data and/or image data is used in one embodiment to determine an optimal elevation beam pattern. Based on data acquired by user and/or automatic variation of the elevation beam pattern, parameter values are calculated for a scan line, scan plane (e.g. image), scan volume or portions thereof. For example, a parameter value is calculated for each two-dimensional image where each two-dimensional image is responsive to a different elevation beam pattern. Any of various parameters are calculated, such as a maximum brightness. In one embodiment, each image associated a different elevation beam pattern is high pass filtered or otherwise processed to identify gradients. A threshold is applied to the filtered data. Data above the threshold likely represent edges. The number of data points corresponding to edges (e.g. the number of remaining data points after thresholding) is summed. Another parameter is a speckle statistic, such as the ratio of the mean value to a standard deviation. Other parameters or combinations of different parameters may be used.

The elevation beam pattern associated with the desired or optimal parameter value is selected. For example, in the embodiment above, the elevation beam pattern associated with the largest number of edge data points is used for further imaging. Minimum, mean or other relationships between different parameter values may be used for selecting the optimal elevation beam pattern. The selected elevation beam pattern is used for subsequent imaging, such as in a diagnosis mode.

Varying the elevation beam pattern is used for any of various applications. For example, varying the elevation beam pattern assists in needle localization during a biopsy or other procedure. To locate a needle, the elevation beam pattern is widened to more likely include the needled in the scan plane. In one embodiment, the user adjusts a knob or other user input to widen the elevation beam thickness to search for the needle. In another embodiment, the user initiates a search mode on the system 10 and the system 10 automatically widens the elevation beam thickness. Once the needle is located, the user adjusts the position of the transducer array 14 to better scan the needle and the elevation beam thickness is narrowed.

Another example application is cardiac wall visualization. Endocardial and epicardial heart boundaries are visualized for assessment of wall motion, ejection fraction and other diagnostic parameters. For both of subjective visualization and user or automatic segmentation or tracing of the heart walls, discontinuous contours or "drop out" of the heart wall in the images are undesirable. By varying the elevation beam pattern, such as the elevation beam thickness, an optimal elevation beam pattern that includes the heart wall over a continuous contour while maximizing the signal-to-noise ratio and resolution is selected. The optimal beam pattern maximizes the border contrast and continuity. The user varies the elevation beam pattern for subjective optimization, or the system 10 varies the elevation beam pattern for a calculated optimization.

In another embodiment, data responsive to multiple different elevation beam patterns is used for diagnosis. The elevation beam pattern is varied to acquire the data, such as data representing the heart walls. For example, optimal elevation beam patterns are selected for two or more frequencies of operation (e.g., transmit and/or receive center frequencies). One possibility is a narrower beam pattern for higher frequencies (e.g., better resolution) and a wider beam pattern for lower frequencies (e.g. more inclusive volume). Other possibilities include the opposite combination of frequency and elevation beam thickness. The data or images are combined for both frequency and spatial compounding, such as averaging, weighted averaging or other filtering. The different elevation beam patterns result in different spatial speckle patterns, so compounding reduces speckle noise. In alternative embodiments, data corresponding to different elevation beam patterns but same frequencies are compounded. The compounding may be performed alternatively or additionally as described in Section II.

Another example application is locating flow within the heart. Using an external transducer to image flow within the heart may be difficult. Imaging through the ribs uses precise placement and orientation of the transducer. Even transesophageal probes may require precise positioning while subject to patient movement. Flow within the heart may show leaking valves or tiny jets of flow, but a narrow elevation beam thickness may miss the small jets of flow. The user or the system 10 varies the elevation beam pattern to more likely include the small jets of flow while maximizing sensitivity. A continuous search pattern for varying the elevation beam pattern may be used where a selected beam pattern is occasionally or periodically tested against other elevation beam patterns.

Additional applications include imaging small non-vascular structures or vessels. Small vessels, cysts, tumors, or other non-vascular structures are more likely to be located by using a larger elevation beam thickness. Once located, the elevation beam thickness is narrowed for higher resolution imaging.

In yet another example application, variation of the elevation beam pattern during an imaging session provides an advantage in contrast agent imaging. High amplitude ultrasound energy destroys contrast agents, such as microspheres. The perfusion, reperfusion, loss of correlation, or other characteristic of contrast agents prior to, during and/or after destruction may provide useful information. By varying the elevation beam pattern, a narrower or a wider plane of contrast agents within a patient are destroyed. For example, a wider elevation beam destroys contrast agents over a wide area, and a narrow elevation beam is used to image within the wide area. By imaging after destruction with the narrower elevation beam, the imaged area is initially freer of contrast agents.

II. Elevation Compounding Embodiment

Frames of data associated with different elevational spatial frequency content are compounded together for generating an image with reduced speckle. Using multi-dimensional transducers, such as 1.25, 1.5, 1.75 and 2D arrays, frames of data associated with a same scan plane are acquired using different elevation apertures. Decorrelation of the speckle between the different frames of data reduces the speckle in the compounded image. Using multi-dimensional arrays may allow for frames of data associated with elevation beam patterns having low side lobe levels, narrow beam width and high signal-to-noise ratio for detecting small lesions. Using larger elevation apertures may also allow better identification of curved specular boundaries. The compounding is responsive to either different elevation beam patterns and thicknesses or the same elevation beam patterns and thicknesses.

Figure 1:
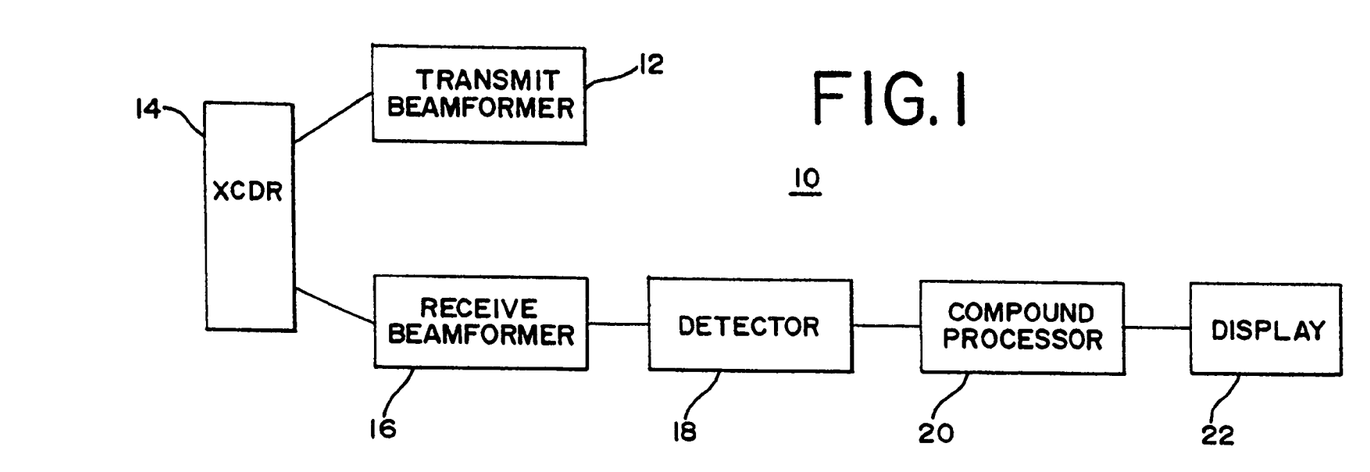
FIG. 1 is a block diagram of one embodiment of an ultrasound system for compounding with different elevation apertures.

FIG. 1 shows an ultrasound system 10 of one embodiment for acquiring ultrasound data with reduced speckle. The system 10 includes a transmitter 12, a transducer 14, a receive beamformer 16, a detector 18, a compound processor 20 and a display 22. Additional, different or fewer components may be provided, such as providing the compound processor 20 and display 22 separately as a computer workstation connected with a source of frames of ultrasound data.

The transmitter 12 comprises a transmit beamformer, such as one or more waveform generators operable to provide delayed and apodized waveforms to the transducer 14. For example, a plurality of memories, amplifiers and other digital and/or analog circuits function in separate channels for focusing the acoustic energy generated by the transducer 14. In alternative embodiments, the transmitter 12 comprises a single channel or a transmitter for generating a plane wave. The transmitter 12 generates electrical signals in successive transmit events. Each transmit event is associated with transmitting acoustic energy into the patient for subsequent receiving of echo signals.

The transmitter 12 includes a plurality of switches for selectively connecting various transmit channels to specific rows or elements of the transducer 14. In alternative embodiments, the switches, such as transistors or microelectromechanical switches are provided in the transducer 14. Additional switches may be provided for switchably connecting either of transmit channels or receive channels to any of the various elements of the transducer 14. The switches allow selection of different apertures, such as different elevation apertures.

The transducer 14 comprises an array of piezoelectric or microelectromechanical elements for transducing between acoustic and electrical energies. The array of elements of the transducer 14 is configured as a multi-dimensional transducer array, such as an N×M array of elements where N and M are greater than 1. The multi-dimensional array has at least two elevation spaced rows of elements. For example, the transducer 14 comprises a 1.25D, 1.5D, 1.75D, or 2D array. A 1.25D array comprises two or more elevationally spaced rows of elements where no relative delay is provided between each of the rows, such as where either a center row or all rows of elements are connected to the same transmit beamformer channels. A 1.5D array comprises three or more elevationally spaced rows of elements where a center and two electrically connected outside or outer rows independently connect to two sets of system channels. All of the rows may be switchably connected to a same set of system channels. A 1.75D array comprises a plurality of elevationally spaced rows that are each independently connectable to sets of system channels, but some switching interconnecting elements of the various elevationally spaced rows may be provided. A two-dimensional array is similar to a 1.75D array, but has a larger number of elevationally spaced rows, such as forming a square array.

The receiver 16 comprises a receive beamformer or other device operable to isolate electrical signals representing acoustical signals from specific spatial locations. In one embodiment, the receiver 16 comprises a plurality of amplifiers, delays and a summer. The amplifiers apply apodization, the delays apply relative delays for focusing and the summer sums the signals from a plurality of elements or channels to form a sample or signal representing a single spatial location. The receiver 16 operates dynamically to change the focus using the apodization and delay profile during a receive event to focus along one or more scan lines.

In one embodiment, the receiver 16 includes separate receive channels or beamformers for connecting to two different apertures at a same time. For example, the receiver 16 connects with two different elevationally spaced apertures, such as connecting with different rows or combinations of rows of elements. The separate apertures may include common elements or rows. The common elements or rows connect with two or more receive channels. In response to a first transmit event, the receiver 16 is operable to receive signals from the two different apertures, and output multiple samples or signals representing the same spatial locations. For a given spatial location, two samples or signals are provided, each associated with a different elevation aperture. In alternative embodiments, the receiver 16 is operable to receive through a single aperture in response to the transmit event. In yet other alternative embodiments, the receiver 16 is operable to receive through three or more separate apertures in response to a single transmit event.

In one embodiment, the receiver 16 includes a filter, such as a baseband filter, a finite impulse response filter, and infinite impulse response filter, a processor implemented filter, an analog implemented filter or other filtering device operable to isolate information at a band of frequencies. In one embodiment, the filter is programmable to select between different possible frequency bands, but a non-programmable filter or a selection of set filters may be provided. The filter is operable to isolate data at different frequency bands, such as isolating information associated with a harmonic (e.g. second harmonic) of a fundamental transmit frequency or information at the fundamental transmit frequency. In one embodiment, two or more separate filters are provided for substantially simultaneously isolating information at two different frequency bands from the same or different apertures. As another example, the filter is operable to isolate information at one fundamental frequency in response to one transmit event and at another or different fundamental frequency in response to a different transmit event.

The transmitter 12 and the receiver 16 are operable to acquire data representing a region of the patient. Any of various scan formats may be used, such as linear, sector, Vector®, curvilinear, other scan formats, and combinations thereof. By maintaining the transducer 14 in one substantially same position, data associated with two different elevation apertures representing a same spatial location or spatial locations within a same scan plane are acquired. Substantially is used with position to account for motion of the patient, breathing by the patient, or unintentional motion by an operator holding the transducer 14. Using electrical or mechanical focus along the elevation dimension, the transducer 14 is operable to transmit and receive along scan lines in a same scan plane from the different apertures. For example, one elevation aperture comprises a left or bottom aperture of a bottom row and a center row of elevationally spaced elements and a second aperture comprises a right or top aperture of a top row and the center row of elevationally spaced elements. The left (i.e. bottom) aperture and right (i.e. top) aperture overlap, both using the center row of elements. Using either a mechanical or electrical focus, both the left and right (i.e. bottom and top) overlapping apertures transmit and receive within the same scan plane. For example, the transmit focus point and the dynamic receive focal points are within the same scan plane. In alternative embodiments, the elevationally spaced rows are close enough together relative to the beam width that no or minimal mechanical or electrical focus provides for scanning within a same scan plane.

Figure 2:
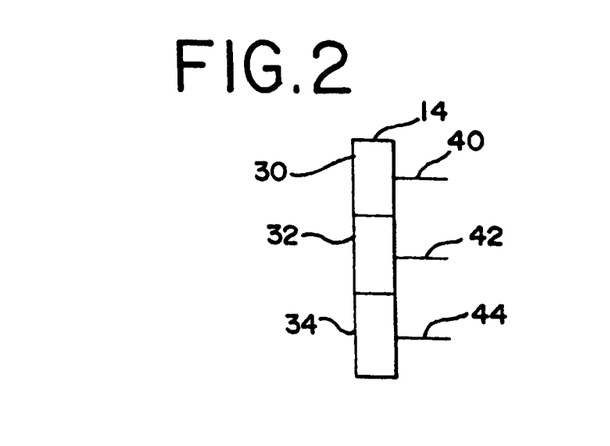
FIG. 2 is a graphical representation of one embodiment of a cross section of a multi-dimensional transducer array.

FIG. 2 shows one embodiment of a cross-section of the multi-dimensional transducer 14 with three elevationally spaced rows 30, 32, and 34 of elements. Three elevationally spaced rows are provided, but two, four or more elevationally spaced rows may be used. Any number of elements may be positioned within a row on the azimuthal dimension. A signal line 40, 42 and 44 connects with each of the elements such as the elevationally spaced elements 30, 32 and 34, respectively. The elevation aperture is responsive to the interconnection of the signal lines 40, 42 and 44 with system channels. For example, where the transducer 14 is a 1.25D array, the center row 32 comprises one elevation aperture by connecting the signal line 42 to a system channel. A second elevational spaced aperture is provided by connecting all of the rows 30, 32 and 34 and the associated signal lines 40, 42, and 44 together to a same system channel. As another example, a 1.5D array provides for the center row 32 and associated signal lines 42 as one aperture. A second elevational aperture comprises the outer rows 30 and 34 and associated signal lines 40 and 44 switched together to a same system channel. All three rows 30, 32, 34 may be switched together in an alternative embodiment. As yet another example for a 1.75D or 2D array, each of the rows 30, 32 and 34 and associated signal lines 40, 42 and 44 are independently connectable to different system channels, but may be switched together. Any one or combination of two or more of the rows 30, 32 and 34 define an elevation aperture. Each of multiple rows in a given elevation aperture may either be switched together to connect the same system channel or connect independently to separate system channels.

The detector 18 comprises a B-mode detector, Doppler detector, flow detector or other circuit for detecting signal characteristics, such as intensity, tissue or fluid energy, tissue or fluid velocity, or tissue or fluid variance. Frames of data responsive to different elevation apertures but representing spatial locations in a same scan plane are input to the detector 18. The detector 18 outputs frames of detected data representing the same scan plane but responsive to different elevation apertures. Where the receiver 16 is operable to output two frames of data representing the scan plane but responsive to different elevation apertures at substantially a same time, the detector 18 includes a buffer for sequentially detecting from the frames of data or includes parallel processing paths for substantially simultaneously detecting from the different frames of data.

The compound processor 20 comprises a general processor, a digital signal processor, an application specific integrated circuit, a summer and multipliers, a summer, a filter, an analog device, a digital device, a memory or combinations thereof. The compound processor 20 receives two or more frames of detected data representing a same scan plane. Where the two frames of data are provided sequentially, a buffer or other memory device stores at least one of the frames of data so that the frames are available for compounding. The compound processor 20 compounds detected data, but data prior to detection may alternatively be compounded. The detected data is either scan converted or in a scan format. The compound processor 20 implements an averaging of data representing same spatial locations within the scan plane. Weighted averaging, lookup table combination, linear, nonlinear or other functions for combining two or more data representing a same spatial location into a single output value may be used.

The display 22 comprises a CRT, monitor, LCD, flat screen or other device for displaying an image responsive to two different elevation apertures. The display 22 may also include a scan converter for converting from a scan format to a display or Cartesian coordinate format. The image has reduced speckle as compared to an image generated without compounding of frames of data responsive to different elevation apertures.

Figure 3:
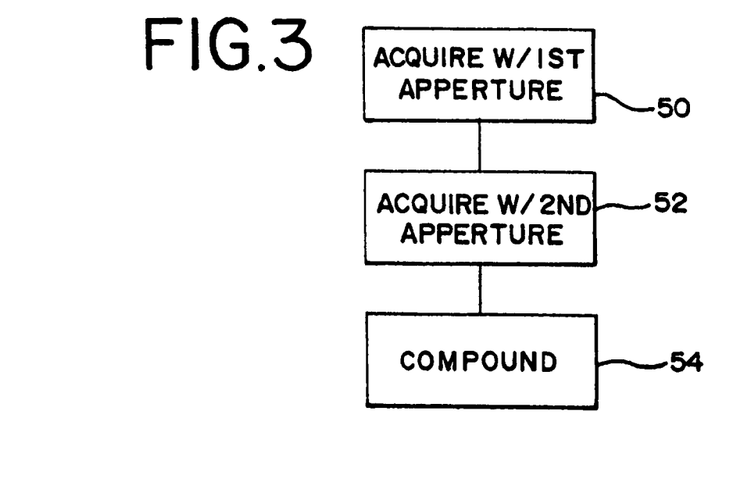
FIG. 3 is a flowchart diagram of one embodiment of a method for reducing speckle.

FIG. 3 is a flow chart representing one embodiment of a method for acquiring ultrasound data with reduced speckle. Multiple frames of data of a target are obtained in response to different elevation apertures of a non-moving multi-dimensional transducer array. For example, data associated with first and second elevation apertures are acquired in acts 50 and 52. The data is then compounded in act 54. Different frames of data are combined to form an elevationally compounded image. A frame of data includes one or more of image data, scan converted data, detected data, incoherent data or other collection of data representing an area at a given time or range of times.

Each frame of data associated with a different elevation aperture of the multi-dimensional transducer array represents the same scan plane. Using electronic or mechanical focus, the elevation width of each beam responsive to each of the different elevation apertures sufficiently ride to insonify the same scan plane or same spatial location. Full decorrelation between component beams or two-way response associated with the different elevation apertures is provided where the spectrum of the component beams is separated by about 6 dB of bandwidth. More separation may not further reduce speckle variance but may reduce the bandwidth of the component beams given that the total bandwidth is limited by the physical size of the aperture.

In one embodiment, the elevation beam pattern of the two-way response has low side lobes and a narrow beam width for a high signal-to-noise ratio. Wider elevation apertures provide increased contrast resolution and better signal-to-noise ratios. A large transmit elevation aperture is desired for harmonic imaging. A continuous elevation aperture provides for a well-defined or predictable beam pattern and avoids or minimizes tissue aberration artifacts.

The frames of data are acquired sequentially, such as transmitting and receiving with a first elevation aperture subsequent to transmitting and receiving with a second aperture. In other embodiments, acoustic energy is transmitted from the multi-dimensional transducer 14 in a first event and the frames of data associated with the different elevation apertures are acquired substantially simultaneously or in response to the same transmit event. The frames of data are then separately receive beamformed to generate the two different frames of data. Since the receive apertures are two different elevation apertures, the overall two-way response or equivalent apertures are different even with the same transmit aperture.

For either of sequential or simultaneous acquisition, the transmit aperture used may be the same as one of either of the two different receive elevation apertures or may be yet a third or different elevation aperture. Better signal-to-noise ratio is provided by transmitting from the entire elevation aperture. The whole elevation aperture may be used with a tapered elevation apodization for better near field performance and lower side lobes, but may be equally apodized across the elevation aperture. For better near field performance, the center row of elements or a grouping of center rows of elements are used for the transmit aperture.

In one embodiment, the different receive apertures include at least one row of elements common to the different elevation apertures. For example, a center row of elements are common to asymmetric or left and right (i.e. bottom and top) overlapping receive apertures. Wide overlapping apertures with left-right (i.e. bottom-top) asymmetry may be used with one, two or more rows of elements in common and one, two or more rows of elements unique to each of the left or right (i.e. bottom or top) apertures. Different receive apertures with no overlap may be used.

For receiving data from two different elevation apertures in response to one transmit event, elevation transmit focal depth aperture overlap may provide an optimal aperture overlap at the transmit focal depth. Around the transmit focus, there is a region of optimal focusing. Receive can be focused at all depths, but each transmit is focused to one or a limited number of depths. The image is optimally focused around the transmit focus. Multiple transmit foci or a line focus extends the region of optimal focus. Deep depth resolution and signal-to-noise ratio may be enhanced with elevation apertures that are a function of the azimuthal focal depth using the sequential transmit and receive acquisition. The elevation extent of the receive apertures or the rows of elements used may change as a function of the selected azimuthal focal depth.

In one embodiment, both of the receive, transmit or receive and transmit elevation apertures are continuous, such as including all rows of elements between the edges of the elevation aperture. For example, an elevation aperture of any one of the rows 30, 32 and 34 of FIG. 2 is a continuous aperture. Left or right (i.e. bottom or top) apertures of rows 30 and 32 or 32 and 34, respectively, are continuous. The entire aperture including rows 30, 32 and 34 is continuous, but rows 30 and 34 connected in an aperture without the center row 32 are not continuous.

The different elevation apertures used as either receive apertures or both transmit and receive apertures vary as a function of the type of transducer 14. For a 1.25D array, a single row of elements is used for one elevation aperture. A second elevationally spaced row is switched with the single row and used as the second elevation aperture. The frame of data associated with the two or more switched together rows has a different spatial frequency content as a result of the 50 percent overlap in the elevation aperture.

For a 1.5D array, one elevation aperture is a center row or rows. The different elevation aperture is the outer rows on each side of the center row or the outer rows and the center row. Different spatial frequency content results from the non-overlapping or partially overlapping elevation apertures. Any of various combinations of transmit and receive apertures may be used, such as transmitting from three rows and receiving on the center row and then transmitting from two outer rows and receiving on the two outer rows.

For a 1.75D or 2D array, any of various combinations of rows or selected single rows are used to form the two different elevation apertures. At least one row of elements is used in one elevation aperture and not in another elevation aperture. For example, one row, such as a bottom row, is used for transmitting and receiving acoustic information. Subsequently, a center row is used to acquire information for another frame of data. A top or another edge row is then used to acquire a third frame of data. Since three different elevation apertures are used, each frame of data is associated with a different spatial frequency content. In alternative embodiments, overlapping apertures, only two apertures, or four or more different elevation apertures may be used. A two-dimensional array may operate similar to a 1.75D array, but with additional elevation spaced rows of elements for use in any given elevation aperture. Any of various combinations of transmit and receive apertures may be used, such as transmitting with all three rows for each of the receptions in the 1.75D example above.

In one embodiment, speckle is reduced using frequency compounding in addition to using different elevation apertures. A first frame of data is acquired in response to one frequency band and the second frame of data is acquired in response to a different frequency band. For example, both frames of data are associated with the same transmit frequency but received at the fundamental frequency and a harmonic of the fundamental frequency. For example, a frame of data acquired using a center row of elements as the elevation aperture is acquired at a fundamental or transmitted frequency band. A second frame of data associated with an elevation aperture of three rows is received at a second harmonic of the fundamental transmit frequency. The harmonic frequencies may be used for imaging added contrast agents or for imaging tissue free of added contrast agents for an entire imaging session. As another example, the first frame of data is associated with a harmonic of a first fundamental transmit frequency, and a second frame of data is associated with a same or different harmonic of a different or same fundamental transmit frequency. In alternative embodiments, the frames of data are acquired in response to the same transmit and receive frequencies and the same bandwidths.

In act 54, the first and second frames of data are compounded for each of a plurality of spatial locations. A datum from one frame of data is compounded with a datum from the other frame of data for each spatial location. The compounding comprises a summation, multiplication, linear, nonlinear or other combination function. For example, the data is averaged. A weighted averaging may be used, such as weighting a frame of data associated with higher resolution, such as harmonic frequency data, more greatly than other frames of data. Two, three or a greater number of frames of data may be compounded.

The data compounded comprises detected pre-scan converted data. Where a same scan format is used for each frame of data, the same spatial locations are represented in each frame of data. Where different scan formats are used, the compounding may involve interpolation, extrapolation, spatial averaging or selection of data representing a location closest to the desired spatial location. In yet other alternative embodiments, correlation techniques are used for spatially aligning one frame of data relative to another frame of data to counteract unintentional movement of the transducer 14 or the patient. In yet other alternative embodiments, scan converted data is compounded. In other embodiments, data is compounded prior to detection with or without accounting for relative phase shifts or the coherence of the data.

In one embodiment, a running average of frames of data associated with different elevation apertures outputs compound images or frames of data at a same rate as the frame acquisition rate. For example, the different elevation apertures are repeated. For any two or three sequentially acquired frames of data, each frame is associated with a different elevation aperture. A moving window is then applied to the frames of data for compounding. By using parallel receive beamformation techniques, such as receiving using two different elevation apertures in response to a same transmit event, compounding is provided without reducing the acquisition rate and associated output frame rate or display rate. In alternative embodiments, the compounded image frames are output at a slower rate than the acquisition rate, such as associated with inputting two frames of data associated with different elevation apertures and outputting a single compound frame. The two input frames are then discarded, and the next compounded image frame is responsive to two different frames of data.

In one embodiment, a transducer with a frequency dependent elevation aperture is used to scan a same plane with different bandwidths. For example, the transducers disclosed in Hanafy, U.S. Pat. No. 6,043,589 "Two Dimensional Transducer Array and the Method of Manufacture thereof", in Hossack et al., U.S. Pat. No. 5,678,554 "Ultrasound Transducer for Multiple Focusing and Method for Manufacture Thereof" and in Ustuner U.S. Pat. No. 6,057,632 "Frequency and Bandwidth Controlled Ultrasound Transducer", the disclosures of which are incorporated herein by reference are used with different frequency bands acquire different data representing a scan plane. In another embodiment, the frequency responsive dual elevation element transducer disclosed in (U.S. application Ser. No. 60/386,324), the disclosure of which is incorporated herein by reference, is used with different frequencies or bandwidths to acquire different data representing a same scan plane.

While the invention has been described above by reference to various embodiments, it should be understood that many changes and modifications can be made without departing from the scope of the invention. For example, any of various combinations of different or same transmit and receive apertures, focal profiles and/or apodization profiles may be provided. The different elevation beam patterns may be used in combination with the same or different azimuth beam patterns for any one or all of the elevation spaced rows of the multidimensional transducer array. Other elevation or azimuth scanning techniques or other techniques for reducing speckle may be used in combination with the elevation beam pattern variation disclosed herein.

It is therefore intended that the foregoing detailed description be understood as an illustration of the presently preferred embodiments of the invention, and not as a definition of the invention. It is only the following claims, including all equivalents, which are intended to define the scope of this invention.

What is claimed is:

1. A method for ultrasound imaging with a multi-dimensional transducer array, the method comprising:
    (a) scanning along at least a first scan line relative to the multi-dimensional transducer array in response to a first elevation beam pattern, the scanning with the first elevation beam being at a first elevation focal region;
    (b) scanning along at least the first scan line in response to a second elevation beam pattern, the second elevation beam pattern different than the first elevation beam pattern, and the scanning with the second elevation beam being at the first elevation focal region;
    wherein (a) and (b) occur during a same scanning session; and
    (c) generating images responsive to the first and second elevation beam patterns, the images being generated without compounding of data.

2. The method of claim 1 wherein (a) and (b) comprises varying an elevation beam thickness during the scanning session.

3. The method of claim 2 wherein (a) and (b) comprise scanning with a wider elevation beam thickness at a focal region in (a) than in (b), (a) occurring prior to (b).

4. The method of claim 1 further comprising:
    (c) varying between the first and second elevation beam patterns in response to user input.

5. The method of claim 1 wherein (a) and (b) comprise varying between at least three elevation beam thicknesses;

further comprising:

(c) subsequently imaging during the scanning session in response to user selection of one of the at least three elevation beam thicknesses.

6. The method of claim 1 wherein the first elevation beam pattern has a wider thickness at a focal region than the second elevation ben pattern.

7. The method of claim 1 wherein (a) and (b) both comprise scanning with a different elevation aperture.

8. A method for ultrasound imaging with a multi-dimensional transducer array, the method comprising:

(a) scanning along at least a first scan line relative to the multi-dimensional transducer array in response to a first elevation beam pattern; and (b) scanning along at least the first scan line in response to a second elevation beam pattern, the second elevation beam pattern different than the first elevation beam pattern;

wherein (a) and (b) occur during a same scanning session;

wherein (a) and (b) both comprise scanning with a same elevation aperture.

9. A method for ultrasound imaging with a multi-dimensional transducer array, the method comprising:

(a) scanning along at least a first scan line relative to the multi-dimensional transducer array in response to a first elevation beam pattern; and (b) scanning along at least the first scan line in response to a second elevation beam pattern, the second elevation beam pattern different than the first elevation beam pattern;

wherein (a) and (b) occur during a same scanning session;

wherein (a) comprises scanning in a search mode and (b) comprises scanning in a diagnosis mode; and wherein (a) comprises scanning while moving an aperture and (b) comprises scanning while maintaining a scan position relative to the patient.

10. The method of claim 9 wherein the search mode and the diagnosis modes are associated with different thicknesses.

11. A method for ultrasound imaging with a multi-dimensional transducer array, the method comprising:

(a) scanning along at least a first scan line relative to the multi-dimensional transducer array in response to a first elevation beam pattern; and (b) scanning along at least the first scan line in response to a second elevation beam pattern, the second elevation beam pattern different than the first elevation beam pattern;

wherein (a) and (b) occur during a same scanning session and first and second images are generated from the scans of (a) and (b), respectively;

wherein the first elevation beam pattern has a wider thickness at a focal region than the second elevation beam pattern, (a) comprises destroying contrast agents within a first region and (b) comprises scanning for reperfusion of contrast agents within a second region within the first region.

12. A method for ultrasound imaging with a multi-dimensional transducer array, the method comprising:

(a) scanning along at least a first scan line relative to the multi-dimensional transducer array in response to a first elevation beam pattern;

(b) scanning along at least the first scan line in response to a second elevation beam pattern, the second elevation beam pattern different than the first elevation beam pattern;

wherein (a) and (b) occur during a same scanning session;

(c) calculating first and second parameter values responsive to the first and second elevation beam patterns, respectively;

(d) selecting one of the first and second elevation beam patterns as a function of the first and second parameter values; and (e) imaging in response to the selected one of the first and second elevation beam patterns.

13. The method of claim 12 wherein (a) and (b) comprise scanning in response to automatic variation between the first and second elevation beam patterns.

14. A system for ultrasound imaging with different elevation beam patterns, the system comprising:

a multi-dimensional transducer array; and a beamformer connected with the multi-dimensional transducer array, the beamformer operable to form a first beam in response to a first elevation beam pattern, the first beam emanating from the multi-dimensional transducer array at a first location and first angle within a plane and operable to form a second beam in response to a second elevation beam pattern, the second beam emanating from the multi-dimensional transducer array at the first location and first angle in the plane, the first and second beams formed during a single imaging session, the first elevation beam pattern different than the second elevation beam pattern and having a same elevation focal region; and a processor operable to calculate first and second parameter values responsive to the first and second elevation beam patterns, respectively, select one of the first and second elevation beam patterns as a function of the first and second parameter values, and form subsequent beams in response to the selected one of the first and second elevation beam patterns.

15. The system of claim 14 wherein the first beam pattern has a different elevation beam thickness at a focal region than the second beam pattern.

16. The system of claim 14 wherein the beamformer is operable to automatically vary between the first and second elevation beam patterns.

17. A system for ultrasound imaging with different elevation beam patterns, the system comprising:

a multi-dimensional transducer array; and a beamformer connected with the multi-dimensional transducer array, the beamformer operable to form a first beam in response to a first elevation beam pattern, the first beam emanating from the multi-dimensional transducer array at a first location and first angle within a plane and operable to form a second beam in response to a second elevation beam pattern, the second beam emanating from the multi-dimensional transducer array at the first location and first angle in the plane, the first and second beams formed during a single imaging session, the first elevation beam pattern different than the second elevation beam pattern and having a same elevation focal region; and wherein the beamformer is responsive to a search mode, the first elevation beam pattern corresponding to the search mode and the second elevation beam pattern corresponding to a diagnosis mode, the search mode initiated in response to user input; and generating images responsive to the first and second elevation bean patterns without compounding of data.

18. The system of claim 17 further comprising a user input device, use of the first and second elevation beam patterns by the beamformer responsive to user input from the user input device.

19. The system of claim 17 wherein the search mode and the diagnosis modes are associated with different elevation beam thicknesses.

20. A method for ultrasound imaging with a multi-dimensional transducer array, the method comprising:
 (a) positioning the multi-dimensional transducer array adjacent to a target area;
 (b) transmitting acoustic energy with the multi-dimensional transducer array during (a);
 (c) varying an elevation beam pattern during (b) for sequential transmissions; and
 (d) using a first elevation beam pattern during a search mode and subsequently using a second elevation beam pattern in a diagnosis mode, both the search and diagnosis modes being free of compounding data associated with different elevation beam patterns.

21. The method of claim 20 wherein (c) comprises varying a scan plane thickness for sequential scans of the planar area, the scan plane thickness being relative to a focal region.

22. The method of claim 20 wherein the elevation beam pattern varies in response to user input.

23. The method of claim 20 wherein the elevation beam pattern varies automatically.

24. The method of claim 20 further comprising:
 (e) selecting the first elevation beam pattern as a function of data responsive to the second elevation beam pattern, the second elevation beam pattern different than the first elevation beam pattern.

25. The method of claim 24 wherein (e) comprises user selection of the second elevation beam pattern as a function of images responsive to the first and second elevation beam patterns.

26. The method of claim 24 wherein (e) comprises calculating first and second values from data responsive to the first and second elevation bean patterns.

27. The method of claim 20 further comprising:
 (e) generating images responsive to the first and second elevation beam patterns, the images being generated without compounding of data.

28. The method of claim 20 wherein the search mode and the diagnosis modes are associated with different elevation beam thicknesses.

29. The method of claim 20 wherein (a) comprises scanning while moving an aperture in the search mode and scanning while maintaining a scan position relative to the patient in the diagnosis mode.

30. A method for ultrasound imaging with a multi-dimensional transducer array, the method comprising:
 (a) scanning along at least a first scan line relative to the multi-dimensional transducer array in response to a first elevation beam pattern; and
 (b) scanning along at least the first scan line in response to a second elevation beam pattern, the second elevation beam pattern different than the first elevation beam pattern;
 wherein (a) and (b) occur during a same scanning session;
 (c) selecting the second elevation beam pattern as a function of data responsive to (a).

31. The method of claim 30 wherein (c) comprises user selection of the second elevation beam pattern as a function of images responsive to the first elevation beam pattern.

32. The method of claim 30 wherein (c) comprises calculating first and second values from data responsive to the first and second elevation beam patterns.

33. A system for ultrasound imaging with different elevation beam patterns, the system comprising:
 a multi-dimensional transducer array; and
 a beamformer connected with the multi-dimensional transducer array, the beamformer operable to form a first beam in response to a first elevation beam pattern, the first beam emanating from the multi-dimensional transducer array at a first location and first angle within a plane and operable to form a second beam in response to a second elevation beam pattern, the second beam emanating from the multi-dimensional transducer array at the first location and first angle in the plane, the first and second beams formed during a single imaging session, the first elevation beam pattern different than the second elevation beam pattern and having a same elevation focal region; and
 a processor operable to select the second elevation beam pattern as a function of data responsive to the first elevation beam pattern.

* * * * *